US011986609B2

(12) United States Patent
Spanier et al.

(10) Patent No.: US 11,986,609 B2
(45) Date of Patent: May 21, 2024

(54) EXTERNAL DRIVE UNIT FOR AN IMPLANTABLE HEART ASSIST PUMP

(71) Applicant: ECP ENTWICKLUNGSGESELLSCHAFT MBH, Charlottenburg (DE)

(72) Inventors: Gerd Spanier, Berlin (DE); Maxim Daschewski, Berlin (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 1140 days.

(21) Appl. No.: 16/603,527

(22) PCT Filed: Apr. 6, 2018

(86) PCT No.: PCT/EP2018/058941
§ 371 (c)(1),
(2) Date: Oct. 7, 2019

(87) PCT Pub. No.: WO2018/185330
PCT Pub. Date: Oct. 11, 2018

(65) Prior Publication Data
US 2020/0390953 A1 Dec. 17, 2020

Related U.S. Application Data

(63) Continuation of application No. 15/482,513, filed on Apr. 7, 2017, now Pat. No. 10,926,013.

(30) Foreign Application Priority Data
Aug. 22, 2017 (EP) .................... 17187358
Aug. 22, 2017 (EP) .................... 17187359

(51) Int. Cl.
A61M 1/00 (2006.01)
A61M 25/02 (2006.01)
(Continued)

(52) U.S. Cl.
CPC ............ A61M 25/02 (2013.01); A61M 60/13 (2021.01); A61M 60/148 (2021.01);
(Continued)

(58) Field of Classification Search
CPC .... A61M 1/122; A61M 1/101; A61M 1/1086; A61M 1/1012; A61M 1/1001;
(Continued)

(56) References Cited

U.S. PATENT DOCUMENTS 4,625,712 A  12/1986  Wampler
4,895,557 A   1/1990  Moise et al.
(Continued)

FOREIGN PATENT DOCUMENTS

JP   2001178816 A   7/2001
JP   2005193005 A   7/2005
(Continued)

OTHER PUBLICATIONS

International Search Report and Written Opinion for Application No. PCT/EP2018/058941 dated Jun. 7, 2018.
(Continued)

Primary Examiner — Deborah L Malamud
(74) Attorney, Agent, or Firm — Botos Churchill IP Law LLP

(57) ABSTRACT

An external drive unit for an implantable heart assist pump is provided. The drive unit comprises a motor housing, a transcutaneous drive shaft and a motor for driving the heart assist pump. The motor is connectable to the heart assist pump via the drive shaft, and the motor is arranged inside the motor housing. The drive unit further comprises a catheter surrounding the drive shaft and a purge line for injecting a purge medium into a lumen of the catheter or into a space between the catheter and the drive shaft. The purge line is in thermal contact with an outer surface of the motor housing
(Continued)

Figure 1:
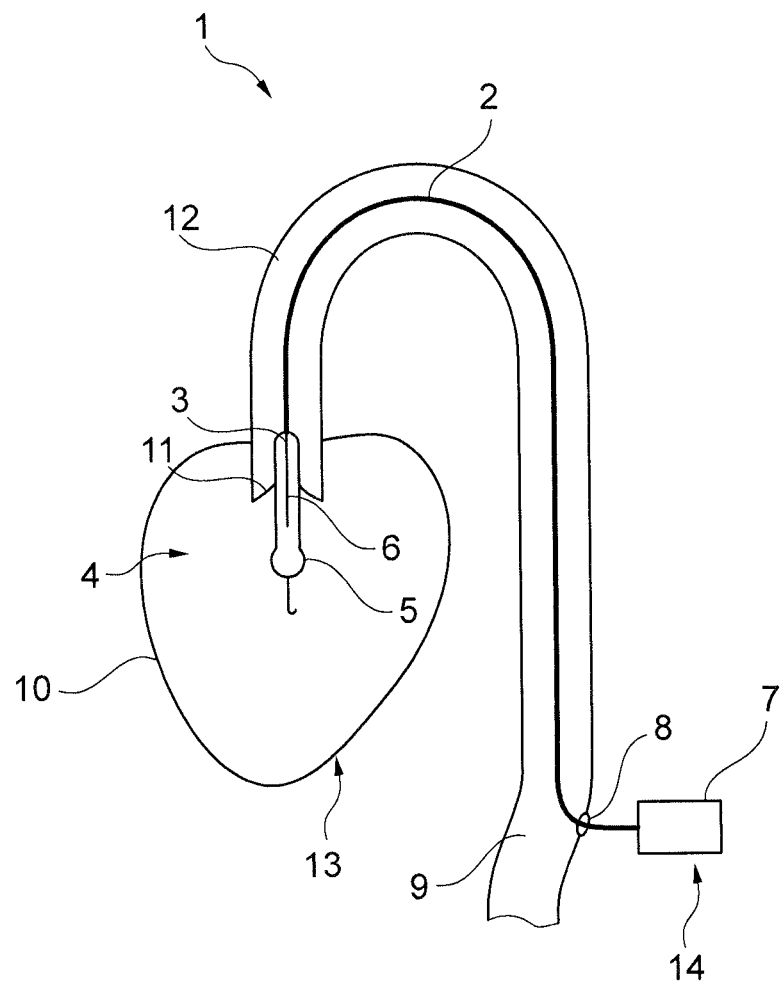

and/or with an outer surface of a proximal section of the catheter. Due to the thermal contact heat is transferred from the outer surface of the catheter in the proximal section and/or from the outer surface of the motor housing to the purge medium.

18 Claims, 9 Drawing Sheets

(51) Int. Cl.
 *A61M 60/13* (2021.01)
 *A61M 60/148* (2021.01)
 *A61M 60/237* (2021.01)
 *A61M 60/414* (2021.01)
 *A61M 60/825* (2021.01)
 *A61M 60/829* (2021.01)
 *A61M 60/871* (2021.01)
 *A61M 60/88* (2021.01)

(52) U.S. Cl.
 CPC ........ *A61M 60/237* (2021.01); *A61M 60/414* (2021.01); *A61M 60/825* (2021.01); *A61M 60/829* (2021.01); *A61M 60/871* (2021.01); *A61M 60/88* (2021.01); *A61M 2025/0266* (2013.01); *A61M 2205/04* (2013.01); *A61M 2205/3666* (2013.01); *A61M 2205/8262* (2013.01)

(58) Field of Classification Search
 CPC ........ A61M 1/1029; A61M 2202/0413; A61M 2205/04; A61M 2205/33; A61M 2205/3576; A61M 2205/36; A61B 2018/00577; A61B 18/00; A61B 18/08; A61B 18/12; A61B 5/0031; B29L 2031/7496; B29L 2031/753; B29L 2031/7532; B29L 2031/7534; A61F 2/06; A61F 7/00; H05B 1/025
 See application file for complete search history.

(56) References Cited

U.S. PATENT DOCUMENTS

| | | | |
|---|---|---|---|
| 5,282,849 A | 2/1994 | Kolff et al. | |
| 5,947,892 A | 9/1999 | Benkowski et al. | |
| 8,449,443 B2 * | 5/2013 | Rodefeld | A61M 60/221 600/16 |
| 8,489,190 B2 | 7/2013 | Pfeffer et al. | |
| 2006/0247738 A1 | 11/2006 | Schmeling et al. | |
| 2007/0106274 A1 | 5/2007 | Ayre et al. | |
| 2015/0073509 A1 | 3/2015 | Kallmyer et al. | |
| 2016/0123826 A1 | 5/2016 | Gardner et al. | |
| 2016/0213827 A1 | 7/2016 | Tanner et al. | |

FOREIGN PATENT DOCUMENTS

| | | |
|---|---|---|
| JP | 2020512899 A | 4/2020 |
| WO | 8905668 A2 | 6/1989 |
| WO | 2010124882 A1 | 11/2010 |
| WO | 2016118777 A1 | 7/2016 |
| WO | 2016118781 A2 | 7/2016 |
| WO | 2018185331 A1 | 10/2018 |

OTHER PUBLICATIONS

European Search Report for EP Application No. 17187359.9 dated Jan. 22, 2018 (3 pages).
International Search Report and Written Opinion for Application No. PCT/EP2018/058942 dated Jun. 27, 2018 (13 pages).
Written Opinion for Singapore Application No. 11201909157P dated Jan. 7, 2021, 6 pp.
Notice for Eligibility to Grant and Examination Report issued in corresponding Singapore Patent Application No. 11201909194T dated Oct. 3, 2022 (6 pp.).
Office Action from corresponding CN Application No. 201880023382.6 dated Jul. 11, 2022, (11 pages).
Office Action for corresponding IL Application No. 269815 dated Jun. 30, 2022 (3 pages).
Office Action from corresponding European Application No. 22187906.7-1113 dated Oct. 31, 2022 (10 pages).
Office Action issued in corresponding Japanese Patent Application No. 2019-555018 dated May 10, 2022 (14 pp.).
Office Action from corresponding Australian Application No. 2018248903 dated Dec. 5, 2022 (3 pp.).
Office Action issued in corresponding Chinese Patent Application No. 2018800233826 dated Nov. 16, 2022, (16 pp.).
Office Action issued in corresponding Chinese Patent Application No. 201880023382.6 dated Nov. 3, 2021, 14 pp.
Office Action issued in corresponding Chinese Patent Application No. 2018800238162.2 dated Jan. 6, 2022, 20 pp.
Office Action issued in corresponding Indian Patent Application No. 201937043708 dated Feb. 7, 2022, 6 pp.
Office Action issued in corresponding Indian Patent Application No. 201937043709 dated Feb. 10, 2022, 6 pp.
Griffith, J.M. et al., "Human Skin Temperature Response to Absorbed Thermal Power" (SPIE Proceedings—The International Society for Optical Engineering 3037:129-134, Mar. 1997).
Office Action from Chinese Patent Application No. 2018800233826, dated Mar. 30, 2023 (16 pp.).
Extended European Search Report from European Patent Application No. 23157183.7, dated Jun. 13, 2023 (7 pp.).
Office Action from corresponding Japanese Patent Application No. 2023-009125 dated Nov. 7, 2023 (8 pp.).
Office Action from corresponding Korean Patent Application No. 10-2023-7038074 dated Dec. 8, 2023 (11 pp.).
Office Action dated Dec. 8, 2023 for KR Appln. No. 10-2023-7039581, (15 pp.).

* cited by examiner

EXTERNAL DRIVE UNIT FOR AN IMPLANTABLE HEART ASSIST PUMP

CROSS-REFERENCE TO RELATED APPLICATIONS

This application is a United States National Stage filing under 35 U.S.C. § 371 of International Application No. PCT/EP2018/058941, filed Apr. 6, 2018, which claims priority to U.S. application Ser. No. 15,482,513, filed Apr. 7, 2017, European Patent Application Nos. 17187359.9, filed Aug. 22, 2017, and 17187358.1, filed Aug. 22, 2017. The contents of each of each of the foregoing applications are hereby incorporated by reference in their entirety. International Application No. PCT/EP2018/058941was published under PCT Article 21(2) in English.

The present application relates to the field of medical technology. The application relates to an external drive unit for an implantable heart assist pump and to a heart assist device comprising the drive unit and the implantable heart assist pump. The present application is related to assignee's U.S. patent application Ser. No. 15/482,513, filed Apr. 7, 2017, entitled "Methods and Systems for an External Drive Unit for an Implantable Heart Assist Pump", which is hereby incorporated by reference.

Heart assist devices for assisting a heart function of a patient are known from the state of the art. Such devices may comprise an implantable blood pump, which may be inserted into a ventricle of the heart by minimally invasive means. Further, an external (or extracorporal) motor may be supplied to drive the blood pump. The motor may be connected with the blood pump via a transcutaneous and flexible drive shaft which may be rotatably mounted inside a transcutaneous catheter. The implantable components of the device may be inserted via a puncture site in a patient's groin. A related device is described, e.g., in U.S. Pat. No. 8,489,190 B2.

For such heart assist devices problems may arise relating to heat dissipated by the external motor. In some applications, the motor may be disposed close to the patient's body, in particular close to the patient's leg, while the blood pump is operated. If heat generated by the motor is not effectively removed the motor may overheat, which may cause malfunction of the motor. In addition, overheating of the motor may constitute a health risk to the patient when a hot housing of the motor contacts the skin of the patient, in particular when the patient is not able to notice the heat and to react appropriately, e.g., due to anesthetic medication. Safe amounts of heat absorption by a human skin have been studied in the context of heat generated by ultrasound and magnetic resonance imaging probes. For example, in "Human Skin Temperature Response to Absorbed Thermal Power" (SPIE Proceedings—The International Society for Optical Engineering 3037:129-134, March 1997) a method is described to determine safe levels of heat absorption.

To prevent the motor of the heart assist device from overheating, the housing of such a motor may be equipped with a multitude of cooling fins so that heat is effectively withdrawn from the motor and dissipated to the surrounding air. However, the amount of heat transferrable to the air may not be sufficient if the motor is operated in an enclosed environment, e.g., underneath a duvet while the patient rests or underneath surgical drapery during surgery. In addition, a surface of the housing with cooling fins may be difficult to clean.

In view of the aforementioned state of the art, it is an objective of the present application to provide an improved external drive unit for an implantable heart assist pump and an improved heart assist device. In particular, it is an objective of the application to provide a drive unit and a heart assist device with an improved heat management. Further, it is an objective of the application to suggest a drive unit which enables a safe and efficient operation of the heart assist device.

These objectives are achieved by an external drive unit with the features of independent claim 1. Optional further features and further developments will become apparent from the dependent claims and the detailed description in conjunction with the accompanying drawings.

The proposed external, i.e., extracorporal, drive unit for an implantable heart assist pump comprises a motor housing, a transcutaneous drive shaft and a motor for driving the heart assist pump. The motor is connectable to the heart assist pump via the drive shaft, and the motor is arranged inside the motor housing. The drive unit further comprises a catheter surrounding the drive shaft and a purge line for injecting a purge medium into a lumen of the catheter or into a space between the catheter and the drive shaft. The purge medium may be a solution, e.g., a glucose solution or saline solution. The purge line is in thermal contact with an outer surface of the motor housing and/or with an outer surface of a proximal section of the catheter. Due to the thermal contact heat may be transferred from the outer surface of the catheter in the proximal section and/or from the outer surface of the motor housing to the purge medium.

The catheter typically comprises a section that is intended to be arranged inside a patient's body and another section that is intended to be arranged outside of the patient's body. The proximal section of the catheter is typically intended to be arranged outside of the patient's body. Injecting the purge medium into the lumen of the catheter or into the space between the catheter and the drive shaft prevents blood from penetrating into the lumen or the space, and from impairing the rotatability of the drive shaft.

In most embodiments, the purge line is configured to guide the purge medium such that it first comes into thermal contact with the outer surface of the motor housing and/or with the outer surface of the proximal section of the catheter and such that the purge medium is afterwards injected into the lumen of the catheter or into the space between the catheter and the drive shaft. The purge medium may additionally be injected into a fluid gap between a stator and a rotor of the motor before it is injected into the lumen of the catheter or into the space between the catheter and the drive shaft and after it comes into thermal contact with the outer surface of the motor housing and/or with the outer surface of the proximal section of the catheter, as described below. The heart assist device and/or the drive unit may comprise a fluid conveyor, e.g., a pump, which is configured to enable a flow of the purge medium in any manner described above and/or below.

During operation of a heart assist device comprising the drive unit, the motor may heat up due to heat dissipation. Further, in some embodiments, also the proximal section of the catheter, which may be arranged close to the motor, may heat up during operation. In particular, during operation heat may be transferred from the motor to the proximal section of the catheter and to a section adjacent to the proximal section of the catheter which may not be covered by a housing and may come into contact with skin of the patient.

Because of the thermal contact of the purge line with the outer surface of the motor and/or with the outer surface of the proximal section of the catheter, heat may be transferred from the motor and/or the proximal section of the catheter to the purge medium in the purge line. Thereby, the motor and/or the proximal section of the catheter may be cooled so that a risk of overheating of the drive unit may be reduced. Especially when the drive unit is arranged underneath a blanket where it may not be sufficiently cooled by ambient air and when the drive unit is in contact with the patient's body such that a risk of burning tissue of the patient is increased, the proposed drive unit improves a safety of operation of the heart assist device.

Compared to the state of the art, the proposed drive unit does not require additional parts, as the purge line serves two purposes at once: First, the purge line leads the purge medium into the patient's body to prevent blood from penetrating into the lumen of the catheter or into the space between the catheter and the drive shaft. Second, the purge line according to the present invention improves the heat management of the drive unit. In addition, the purge medium may be pre-heated by the thermal contact with the motor and/or the proximal section of the catheter. Thereby, a viscosity of the purge medium may be decreased such that a rotatability of the drive shaft is improved. The improvement of the rotatability of the drive shaft may be achieved because the purge medium first comes into thermal contact with the outer surface of the motor housing and/or with the outer surface of the proximal section of the catheter and beacause the purge medium is afterwards injected into the lumen of the catheter or into the space between the catheter and the drive shaft and eventually into the patient. Further, because the purge medium enters the patient only after the thermal contact with the motor housing or the proximal section of the catheter, the initial temperature of the purge medium when coming into thermal contact may be comparably low enabling an efficient heat transfer away from the motor housing and/or the proximal section of the catheter.

During operation of the heart assist device, the outer surface of the motor housing is usually warmer than the outer surface of the proximal section of the catheter. In some embodiments, the purge line is in thermal contact with both the outer surface of the motor housing and the outer surface of the proximal section of the catheter. In these embodiments, cooling the drive unit and pre-heating the purge medium may be particularly efficient. The purge line may be configured to guide the purge medium such that it first comes into thermal contact with the outer surface of the proximal section of the catheter and afterwards comes into thermal contact with the outer surface of the motor housing to allow for a gradual pre-heating of the purge medium and to enable an efficient cooling of the proximal section of the catheter. Then, the purge medium may in some embodiments be injected into a fluid gap of the motor, as explained below. Afterwards, the purge medium may be injected into the lumen of the catheter or into the space between the catheter and the drive shaft.

The catheter may comprise one or more lumen. In some embodiments, the heart assist device may be configured such that the purge medium first flows in a distal direction into the patient's body through one of the lumen of the catheter and then flows back out of the patient's body through another lumen of the catheter. In most embodiments, the lumen of the catheter or the space between the catheter and the drive shaft extends into the proximal section of the catheter. In particular, the lumen or space may extend over an entire length of the proximal section of the catheter and in some embodiments over an entire length of the catheter. In this embodiment, heat may be transferred to the proximal section of the catheter or to the section adjacent to the proximal section via the purge medium in the lumen or space. Hence, cooling the proximal section of the catheter by the purge line may be particularly advantageous in this embodiment.

In most embodiments, the purge line does not form a part of the catheter. In particular, the purge line is not formed by a lumen of the catheter in most embodiments. The purge line may be a separate line that is arranged outside of an outer wall of the catheter.

The purge line is typically fully extracorporal such that it does not comprise any implanted sections. The purge line is typically arranged such that it is in fluid connection with the space or lumen of the catheter. The drive unit typically comprises a purge opening in fluid connection with the space or lumen. The purge line may be attached to the purge opening such that the purge line is in fluid connection with the space or lumen. Typically, during operation of the heart assist device, the purge medium flows in a distal direction in the space or lumen.

The motor may be an electric motor. In some embodiments, the motor comprises a stator and a rotor. The rotor may be connected to the drive shaft. The rotor typically comprises a magnet, in particular a permanent magnet. The stator may comprise a multitude of windings. The stator typically surrounds the rotor, such that a magnetic gap is formed between the magnet of the rotor and the windings of the stator. The rotor may be rotatably mounted. A fluid gap may be formed between the rotor and the stator. The fluid gap may be in fluid connection with the purge opening for injecting the purge medium into the fluid gap. The purge line may be connected to or connectable to the purge opening. The purge medium may be injected into the fluid gap and into the lumen of the catheter or the space between the catheter and the drive shaft. The fluid gap of the motor is usually in fluid connection with a lumen of the catheter or with the space between the catheter and the drive shaft. In typical embodiments, the purge line and the fluid gap are configured to guide the purge medium such that it first comes into thermal contact with the outer surface of the motor housing and/or with the outer surface of the proximal section of the catheter, is afterwards injected into the fluid gap between the rotor and the stator, and is afterwards injected into the lumen of the catheter or into the space between the catheter and the drive shaft.

When unpurged motors are used a seal may be necessary to separate the motor from the space between the catheter and the drive shaft to avoid air from entering into the space and eventually into the patient. The use of a purged motor has the advantage that a complex seal generating friction and separating the motor from the space between the catheter and the drive shaft may not be necessary. Hence, the motor may be easier to fabricate and friction losses may be reduced so that the motor may be operated in a more efficient manner. Further, since a seal is typically prone to failure, when no seal is provided a risk of failure of the heart assist device may be reduced.

When the motor is purged using the purge medium, the motor may be efficiently cooled. Further, because the purge medium is pre-heated due to the thermal contact with the proximal section of the catheter and/or the motor housing, the purge medium already has a reduced viscosity when entering the fluid gap of the motor. Hence, the drive unit reduces friction losses in the fluid gap and/or bearings of the motor and increases an efficiency of the motor.

In some embodiments, the purge line is configured to first guide a flow of the purge medium to an area of thermal contact with the outer surface of the proximal section of the catheter, then to an area of thermal contact with the outer surface of the motor housing, then into the fluid gap between the rotor and the stator, and then into the lumen of the catheter or into the space between the catheter and the drive shaft and/or into the fluid gap of the motor (as described below). Surprisingly, it was found that when a drive unit according to this embodiment is used, the motor current, i.e., the current applied to the windings of the stator, that is necessary to transport a certain amount of blood using the implantable heart assist pump, is independent of the flow rate of the purge medium. In contrast, without a thermal contact between the purge line and the outer surface of the motor housing and/or the outer surface of the proximal section of the catheter, the motor current would increase with an increasing purge flow rate, presumably because the purge medium in the fluid gap is colder for increased flow rates, which leads to an increased viscosity and hence increased friction losses in the motor. The pre-heating of the purge medium according to the present invention then leads to the constant motor current for different purge flow rates. Thereby, the motor current may be advantageously used as a controlling parameter of the heart assist device, because unwanted influences of the purge flow rate on the motor current do not have to be taken into account. Hence, the electronic control of the heart assist device may be significantly simplified.

In some embodiments, the purge line is configured to guide a flow of the purge medium in a proximal direction in an area in which the purge line is in thermal contact with the outer surface of the motor housing and/or with the outer surface of a proximal section of the catheter prior to injection of the purge medium into the lumen of the catheter or into the space between the catheter and the drive shaft. A transfer of heat in such a counter-current flow arrangement is particularly efficient. In this arrangement, the purge medium flows in an opposite direction in the area of thermal contact with the outer surface of the proximal section of the catheter (proximal direction of flow) as compared to in the lumen of the catheter or space between the catheter and the drive line (distal direction of flow), and/or the purge medium flows in an opposite direction in the area of thermal contact with the outer surface of the motor housing (proximal direction of flow) as compared to in the fluid gap between the stator and rotor (distal direction of flow). In particular, the fluid conveyor may be configured such that the purge medium flows distally in the fluid gap.

In some embodiments, the purge line at least partly encircles the motor housing and/or the proximal section of the catheter in the area in which the purge line is in thermal contact with the outer surface of the motor housing and/or with the outer surface of a proximal section of the catheter. By encircling the motor housing and the proximal section of the catheter an area of heat transfer is increased and hence an efficiency of the heat transfer may be improved. Typically, the purge line is in thermal contact with the motor housing and/or with the proximal section of the catheter from multiple sides, e.g., over an angular range of at least 180 degrees. In particular, the purge line may fully encircle the motor housing and/or the proximal section of the catheter over the full angular range.

In some embodiments, the purge line is flexible. The purge line may have a tubular shape and may further have a round cross section. An outer diameter of the purge line may amount to at least 1 mm, preferably at least 2 mm and/or at most 5 mm, preferably at most 3 mm. An inner diameter of the purge line may amount to at least 0.3 mm, preferably at least 0.7 mm, and/or at most 2 mm, preferably at most 1.5 mm. The purge line may contain or be made of a biocompatible material. In some embodiment, the purge line contains or is made of a plastic material such as PU, PEEK or of a metal such as stainless steel. A high thermal conductivity of the material of the purge line can improve the thermal contact between the purge medium and the motor housing and/or the proximal section of the catheter.

The purge line may run around the motor housing and/or the proximal section of the catheter in a helical manner in the area in which the purge line is in thermal contact with the outer surface of the motor housing and/or with the outer surface of a proximal section of the catheter. When the purge line runs in a well-defined helical manner undercut areas inside the purge line may be prevented, and a risk of air pockets remaining in the purge line when the purge line is filled with the purge medium is reduced. For example, for this purpose the purge line may comprise only one serial flow channel for the purge medium and no parallel flow channels. Thereby, a reliable deairing of the purge line may be enabled. For example, the purge line may be wrapped around the motor housing and/or around the proximal section of the catheter. In this embodiment, the drive unit is easy to manufacture. Further, the drive unit may be easily fabricated with the desired heat transfer efficiency simply by choosing a suitable number of turns of the purge line and thereby creating a desired area of heat transfer. In some embodiments, the purge line forms at least 4 turns, preferably at least 8 turns, around the proximal section of the catheter and/or at least 3 turns, preferably at least 5 turns, around the motor housing.

The purge line may be attached to the motor housing and/or to the proximal section of the catheter. In most embodiments, the purge line lies against the outer surface of the motor housing and/or of the proximal section of the catheter in the areas of thermal contact such that the motor housing and/or the proximal section of the catheter directly contact the purge line. However, in other embodiments, a thermally-conductive element may be arranged in between the motor housing and/or the proximal section of the catheter and the purge line. The purge line and the motor housing and/or the proximal section of the catheter may then directly contact the thermally-conductive element. Such an arrangement enables a reliable thermal contact. In some embodiments, the purge line is at least partly integrated into the motor housing. For example, the purge line may be formed in part by a lumen embedded inside the motor housing. An overall thermal conductance (in W/K) between an interior surface of the purge line and an interior surface of the motor housing may amount to at least five times, preferably at least 10 times, an overall thermal conductance between the interior surface of the purge line and an interior surface of the housing of the drive unit. Further, an overall thermal conductance between the interior surface of the purge line and an interior of the motor, in particular the windings of the motor, may amount to at least the overall thermal conductance between the interior surface of the purge line and the interior surface of the motor housing. Such an overall thermal conductance takes into account a series of thermal conductances of the materials arranged between the interior surface of the purge line and the interior surface of the motor housing as well as the cross-sectional areas and the thicknesses and thermal contact conductances. Due to a comparatively high thermal conductivity between the purge line and the housing of the drive unit, heat generated by the motor may be distributed within the housing of the drive unit, e.g., by convection in air, and local hot spots on the housing of the drive unit may be avoided. Further, the interior of the motor is in thermal contact with the motor housing such that heat generated by the motor is transferred to the outer surface of the motor housing. To achieve a sufficient transfer of heat from the fluid gap of the motor to the outer surface of the motor housing, the windings may be cast into a casting material, e.g. epoxy resin, to prevent spaces of air between the fluid gap and the outer surface of the motor housing. In some embodiments, the casting material directly bonds the windings and the motor housing together.

In some embodiments, the drive unit further comprises a heat spreader. The heat spreader may comprise a contact surface configured to contact and/or directly contact and/or lie flat against a skin of a patient. The contact surface is connected or connectable with the motor in a thermally-conductive manner to transfer heat generated by the motor to tissue of the patient.

The drive unit comprising the heat spreader provides a solution which is contrary to the common belief in the state of the art that efficient heat removal from the motor of the heart assist pump has to occur away from the patient as discussed in US 2016/0213827 A1. Instead, efficient heat removal of the proposed drive unit may be achieved at least in part by the transfer of heat to tissue of the patient. Therefore, during operation of the heart assist pump heat may be transferred from the motor to the contact surface of the heat spreader. A thermal conductance of the thermal contact between the motor and the contact surface may be sufficiently large to allow for a transfer of heat that is generated by the motor to tissue of the patient via the heat spreader.

The contact surface may be flat or curved. In typical embodiments, the contact surface is stepless. In a preferred embodiment, the contact surface is flexible to maximize the contact to the tissue. The contact surface may be provided for the transfer of heat from the motor to the tissue. The entire contact surface may come into contact with the skin while the drive unit is in use. The drive unit may further comprise a bottom surface formed by an entirety of all areas of the drive unit designed to come into contact the skin of the patient. The contact surface typically forms a part of the bottom surface. However, in some embodiments, the contact surface forms the entire bottom surface.

The application further relates to the heart assist device comprising the drive unit as described above or below and further comprising the implantable heart assist pump. The heart assist pump may be connected, for example unseparably connected, with the drive shaft of the drive unit. In another embodiment, the motor may be connected to the drive shaft via a coupling, for example via a magnetic clutch.

According to a method of operation of the heart assist device, the drive unit drives the heart assist pump. The purge medium is injected into the lumen of the catheter or into the space between the catheter and the drive shaft. Heat is generated by the motor and transferred to the motor housing. Further, the heat is transferred to the purge line from the outer surface of the motor housing and/or from the outer surface of the proximal section of the catheter.

In some embodiments, the heat spreader is provided and the heat generated by the motor is transferred to the heat spreader. In further embodiments, the contact surface of the heat spreader contacts and/or directly contacts and/or lies flat against the skin of the patient such that heat generated by the motor is transferred to the tissue of the patient. In further embodiments, the contact surface of the heat spreader directly contacts the skin of the patient. However, in some cases another material may be arranged between the skin and the contact surface, e.g., a piece of clothing of the patient.

The drive unit may comprise a housing of the drive unit. The motor housing and/or the proximal section of the catheter may be arranged within the housing of the drive unit. A part of the purge line may run between the motor housing and the housing of the drive unit to achieve the heat transfer to the purge line as described above. Further, a part of the purge line may run between the proximal section of the catheter and the housing of the drive unit to achieve the heat transfer to the purge line as described above. The section adjacent to the proximal section of the catheter may be arranged outside of the housing of the drive unit. Further, the purge line may comprise a section that is arranged outside of the housing of the drive unit. This section is typically attachable to a supply of the purge medium. For simple and cost-efficient fabrication of the drive unit, a diameter of the purge line may be the same in the section that is arranged outside of the housing of the drive unit and in sections that are in thermal contact with motor housing and/or with the proximal section of the catheter.

The heat spreader may be attached to the housing of the drive unit. In typical embodiments, the housing of the drive unit is an external housing that may be at least partly visible when the drive unit is assembled. The heat spreader may be arranged outside of the housing of the drive unit. The heat spreader is configured to enable a conduction of heat from the motor to tissue of the patient. In most embodiments, the heat spreader is a passive component that requires no supply of electrical energy. Further, the heat spreader does not rely on moving parts and/or moving fluids in most embodiments. The heat spreader may be rigidly or movably connected with the housing of the drive unit. In some embodiments, the heat spreader is removably connected with the housing of the drive unit. For example, it may be convenient to implant the heart assist pump in the catheterization lab with the heat spreader disconnected. The housing of the drive unit may serve as a handle of the heart assist device in this situation. After the implantation procedure, the housing of the drive unit may be connected with the heat spreader so that heat generated by the motor may be efficiently transferred to tissue of the patient. The heat may be transferred from the motor to the motor housing. The motor housing may be in thermal contact with the housing of the drive unit so that the heat generated by the motor may be transferred from the motor housing to the housing of the drive unit. Further, this heat may be transferred from the housing of the drive unit to the heat spreader.

The drive unit may comprise a holding means configured to attach the drive unit to a thigh of the patient. When the heart assist device is use, in a typical application scenario at least the bottom surface of the drive unit comes into contact with the skin of the patient. The contact surface may then also come into contact with the skin. The drive unit then allows for a particularly efficient removal of heat from the motor during operation of the motor. Thereby, overheating of the motor may be prevented from occurring.

The heat spreader acts together with the proposed thermal contact of the purge line with the motor housing and/or the proximal section of the catheter in optimizing the heat management of the heart assist device. In many embodiments, a heat transfer from the drive unit to ambient air is not required when the heart assist device is operated. Hence, the heart assist device may be reliably operated without overheating even when the drive unit is covered by a duvet or surgical drapery. In typical embodiments, cooling fins are not needed. Hence, the proposed drive unit may be designed in a comparably compact manner, which improves an ease of attaching the drive unit and a comfort of wear of the drive unit. Further, the amount of heat removed from the motor is foreseeable and not strongly dependent on temperatures of ambient air or flow rates of ambient air. Therefore, a heat management of the drive unit may be controlled in a reliable manner. Also, because the cooling fins are not needed, the housing of the drive unit may have a partly or fully continuous and/or stepless surface. Hence, the drive unit may be easy to clean.

Therefore, the drive unit may be advantageously used in different application scenarios:

First, during implantation of the heart assist device in a catheterization laboratory the motor may be placed above a sterile drapery, because the region underneath the drapery may be considered non-sterile. In this situation, convection of air around the motor is possible, which reduces the risk of overheating. Furthermore, unintended contact of the patient with the motor is unlikely, and a contact of the user (physician) with the motor typically occurs with gloves. The acceptable temperature of the motor is thus higher than in the second application scenario described below. Further, a risk of contamination of the drive unit is relatively high, because the user may touch the motor with contaminated, in particular bloodstained, gloves.

Second, during patient transport or at an intensive care unit it is especially important that the pump keeps its position inside the patient. In this situation, the motor, due to its weight, should be fixed reliably in relation to the puncture site. For this purpose, the motor is usually placed underneath a blanket or duvet. Thus, heat transfer from the motor by convection is not efficient, and a risk of overheating of the motor during operation has to be considered. Further, direct contact of the patient with the pump is likely in this scenario. Hence, the efficient heat transfer from the motor to the purge medium and/or to tissue of the patient as ensured by the drive unit described above or below is highly beneficial. Further, as after a longer time of use the motor may need to be cleaned, the surface geometry that may be obtained with the proposed drive unit is beneficial as compared with designs of heat sinks known from the art, e.g., comprising cooling fins.

The surface area of the contact surface of the heat spreader may be larger than a surface area of a surface of the housing of the drive unit, said surface of the housing of the drive unit being the surface of the housing that faces the patient during operation. The heat spreader may be sized such that it extends beyond the housing of the drive unit. In some embodiments, a surface area of the contact surface is at least 25 $cm^2$, preferably at least 50 $cm^2$ or at least 100 $cm^2$. Typically, the surface area is smaller than 400 $cm^2$. A sufficiently large surface area is necessary to enable an efficient transfer of heat from the motor to tissue of the patient. In addition, a sufficiently large surface area is important to prevent a local overheating of the tissue and damage to the tissue from occurring. An amount of heat transferred to the tissue of the patient is typically at most 80 mW per $cm^2$, preferably at most 60 mW per $cm^2$ or at most 40 mW per $cm^2$, of a surface area of the contact surface. Further, the surface area constitutes an important factor when designing the heat management of the drive unit and enables the motor to be operated at a desired temperature. In most embodiments, during operation of the drive unit a ratio of the surface area of the contact surface and the heat dissipated by the motor is at least 13 $cm^2$/W, preferably 25 $cm^2$/W and especially preferred 50 $cm^2$/W to avoid local overheating of the tissue.

The heat spreader may be flexible at least in areas. Thereby, the contact surface may adapt to a contoured surface of the skin. For example, the contact surface can adapt to a shape of the thigh when the drive unit is attached to the thigh of the patient. Hereby, a comfort of wear of the drive unit may be improved and a thermal contact between the heat spreader and the skin of the patient may be ensured. The heat spreader may be flexible in all areas of the heat spreader.

The heat transferred to the tissue usually does not serve a therapeutic purpose. To enable an efficient transfer of heat from the motor to the tissue of the patient, the heat exchanger may comprise at least a section of a material with a relatively high thermal conductivity. This region may fully extend over the contact surface. The thermal conductivity in this region may be at least 1 W/(m·K), preferably at least 10 W/(m·K), at least 50 W/(m·K), or at least 100 W/(m·K). In a preferred embodiment, the thermal conductivity of the heat spreader is higher in a direction parallel to the contact surface of the heat spreader than perpendicular to the contact surface to ensure that the heat energy is widely spread over the surface and to avoid hot spots.

Since for the safe and efficient transfer of heat from the motor to tissue of the patient a distribution of the heat across the surface area is of primary importance, the weight of the drive unit and the amount of material necessary may be reduced by designing the heat spreader such that it is of a flat shape. Hence, the heat spreader may comprise a thickness of less than 2 cm, in particular less than 1 cm or less than 0.5 cm. For example, the heat spreader may be a foil.

The heat spreader may comprise a thermally conductive layer. The thermally conductive layer may enable a rapid and efficient transfer of heat across the area of the contact surface so that hot spots on the skin are avoided. The heat spreader may further comprise a carrier layer. The carrier layer may have a lower thermal conductivity than the thermally conductive layer. The carrier layer may contain an elastomer and/or plastic. In this manner, the thermally conductive layer, in particular a relatively thin and/or flexible layer, may enable a sufficient transfer of the heat while the carrier layer may supply a sufficient mechanical stability of the heat spreader. The thermally conductive layer may contain a metal, in particular copper, aluminium and/or pyrolytic carbon. In some embodiments, the heat spreader may comprise more than one thermally conductive layer.

In addition, the heat spreader may comprise a biocompatible coating. For example, the contact surface of the heat spreader may comprise a biocompatible coating. The coating may form a part of a bottom surface of the heat spreader or fully form the bottom surface of the heat spreader. The coating may cover and/or enclose the thermally conductive layer. In particular, the coating may be provided if the heat spreader or its thermally conductive layer comprises harmful substances, which may be dissolvable in sweat. The coating may then prevent the harmful substances from reaching the skin of the patient. For example, the biocompatible coating may contain parylene, polyurethane, silicone, PEEK, or a biocompatible, for example an implantable metal. The biocompatible coating may have a thickness of less than 2 mm, preferably less than 0.5 mm or less than 0.1 mm. The biocompatible coating may be identical with the carrier material building a biocompatible carrier.

Further, the motor and/or a motor housing and/or the housing of the drive unit may be elongated. A direction of elongation of the motor and/or of the motor housing and/or the housing of the drive unit may coincide with an axial direction of the thigh when the drive unit is attached to the thigh of the patient. The holding means is typically connected with the housing of the drive unit. The holding means of the drive unit may comprise a strap and/or a hook-and-loop fastening means. The holding means may further comprise an adhesive. An adhesive attachment of the drive unit to the thigh allows for a particularly reliable fixation of the drive unit with respect to the puncture site. In particular, when the drive unit is attached to the thigh of the patient, the adhesive fixation may form an effective holding means that prevents the drive unit from sliding down a tapered portion of the thigh towards the knee. For example, mechanical stress exerted on the puncture site may be reduced by the suggested holding means. In some embodiments, the heat spreader comprises an adhesive surface for attaching the heat spreader to the skin. For example, the heat spreader may be formed by an adhesive patch. According to this embodiment, heat generated by the motor may be transferred to tissue of the patient via the patch. The thermal conductance of the patch may be sufficiently large so that the heat is efficiently transferred to the tissue. The adhesive surface may form a part of the contact surface and/or the entire contact surface. The adhesive may be a biocompatible adhesive as for example well known from adhesive wound closure patches.

Further, the drive unit may comprise a means of fixation to prevent shifting of the drive unit to different positions on the skin of the patient. For example, the means of fixation may comprise rubberized areas. The bottom surface of the drive unit may further comprise nubs.

The heat spreader may comprise openings or recesses, in particular through holes or grooves, to allow for an evaporation of sweat from the skin. The openings or recesses may be at least partially disposed adjacent to the contact surface. In typical embodiments, the heat spreader comprises at least three, at least five or at least eight openings or recesses. During operation of the motor heat transferred to tissue of the patient may result in an enhanced perspiration of the patient. Therefore, the openings or recesses may significantly improve a comfort of wear of the drive unit. To achieve an efficient transfer of vapour to the ambient air, a smallest or uniform diameter of the openings or recesses is typically at least 1 mm or at least 5 mm. A largest or the uniform diameter of the openings or recesses is typically at the most 20 mm or 80 mm.

In some embodiments, the openings are elongated. A ratio of the largest diameter to the smallest diameter may be at least 1.2 or at least 2. In this way, the sweat (in the form of vapour) may be efficiently transferred from the body to the ambient air, while a sufficient mechanical stability and an efficient two-dimensional heat conduction in the heat spreader is ensured. For example, the openings may be elongated such that the openings exhibit a larger diameter in a circumferential direction of the thigh and a smaller diameter in the axial direction of the thigh when the drive unit is attached to the thigh of the patient. If the motor is elongated in the axial direction, the elongation of the holes may allow for the heat to be efficiently transferred in the circumferential direction, while the vapour is efficiently removed from the skin.

In some embodiments, the heat spreader comprises pores to allow for vapourized sweat to be transferred from the skin to ambient air. The heat spreader may comprise a membrane with the pores. The pores may have diameter of at least 0.02 μm and/or at most 0.3 μm.

The heat spreader may comprise a sweat absorbent material, in particular a textile or cotton. The sweat absorbent material may form a part of the bottom surface of the heat spreader. The sweat absorbent material may absorb sweat from the skin of the patient and hence improve the comfort of wear of the drive unit.

In some embodiments, the heat spreader comprises a heat pipe. The heat pipe may be flat. For example, the heat pipe may be a heat diffusor. Typically, a bottom surface of the heat pipe comes into contact with the skin of the patient. In other embodiments, a heat pipe may be arranged between and connected with the motor and the heat spreader. A top surface of the heat pipe may be in thermal contact with the motor. The heat pipe may enable an efficient transfer of heat from the motor to the tissue or to the contact surface.

Friction losses in the purge medium may be expected to lead to a reduced efficiency of the purged motor as compared with an un-purged motor. Surprisingly, a disadvantageously low efficiency of the motor may be circumvented by any one of the features described above or below and by a combination of these features. A width of the fluid gap may be at least 0.1 mm, preferably at least 0.2 mm, and/or at most 1 mm, preferably at most 0.5 or at most 0.3 mm. It has to be considered that a minimal size of the magnetic gap is limited by a size of the fluid gap. Typically, the rotor and/or the stator comprise a sleeve or a coating which may delimit the fluid gap. The delimiting surfaces of the fluid gap may be smooth and/or stepless and may avoid undercut surfaces to ensure a reliable venting process. Hereby, the rotor magnet and/or the stator windings may be protected from a corrosive effect of the purge medium. As a consequence, the magnetic gap is typically larger than the fluid gap. Although the magnetic losses are expected to increase with increasing width of the fluid (and magnetic) gap, it was surprisingly found that the relatively large width of the fluid gap leads to an overall improvement of the efficiency of the motor. This improvement is related to a reduction of the friction losses in the purge medium.

As explained above, the proposed drive unit allows for a precise control of the heat management of the heart assist device in various application scenarios. In particular, the temperature of the purge medium in the fluid gap may be precisely controllable. This effect may be achieved by the pre-heating of the purge medium due to the thermal contact with the outer surface of the proximal section of the catheter and/or the outer surface of the motor housing or by the heat removal from the motor to the purge line and/or to the heat spreader. In typical embodiments, the temperature of the purge medium in the fluid gap is at least 50° C., preferably at least 60° C., in a steady state of operation. Further, the temperature of the purge medium in the fluid gap is at most 100° C., preferably at most 90° C., in a steady state of operation. By controlling the temperature of the purge medium accordingly, the viscosity of the purge medium may be decreased while the temperature of the purge medium may be kept safe for the patient and the purge medium is prevented from boiling. Therefore, the motor may be operated in a particularly efficient manner by controlling the temperature of the purge medium such that the friction losses in the fluid are low.

To precisely control the temperature of the purge fluid, the temperature of the pre-heated purge medium as well as the heat transfer between the fluid gap and the skin of the patient and/or between the fluid gap and the purge line has to be analysed and coordinated. For example, a heat transfer from the fluid gap to the purge line may be influenced by a material of the motor housing. The motor housing may contain or be made of a metal, e.g., stainless steel or aluminium. The windings of the motor may be arranged inside the motor housing in some embodiments. In some embodiments, the motor housing is in part or completely formed by a plastic casting material encapsulating the windings. The windings may comprise one or more copper wires. Further, a heat transfer from the fluid gap to the heat spreader may be influenced by a material of the housing of the drive unit. The housing of the drive unit may contain or be made of a plastic material, e.g., PEEK or ABS. The plastic material is particularly suited to enable operation of the motor in the desired temperature range. In some embodiments, the housing of the drive unit is shaped such that it may be used as a handle of the drive unit.

In some embodiments, the drive unit comprises a thermal insulator arranged between the purge line and the housing of the drive unit. The thermal insulator may be arranged between the area of thermal contact with the proximal section of the catheter and the housing of the drive unit. Additionally or alternatively, the thermal insulator may be arranged between the area of thermal contact with the motor housing and the housing of the drive unit. The thermal insulator may enclose the purge line. In addition, the thermal insulator may be of a tubular shape. The thermal insulator may comprise plastic material, in particular foamed plastic material. In some embodiments, an air gap or a vacuum gap is formed between the purge line and the housing of the drive unit to achieve a thermal insulation between any or both of the regions of thermal contact and the housing of the drive unit. The air gap may enable an even distribution of heat generated by the motor within the housing of the drive unit by convection, so that local hot spots on the housing of the drive unit are avoided. Further, the purge line may be partly enclosed within heat shrink tubing in the area of thermal contact with the motor housing and/or with the proximal section of the catheter so that the thermal contact is improved.

According to some embodiments of the heart assist device, the drive unit may or may not comprise a purge line in thermal contact with the proximal section of the catheter and/or with the motor housing. Further, the drive unit may not comprise a heat spreader as described above or below and/or the drive unit may comprise a heat spreader which is not intended to be brought in contact with the skin of the patient. A means of heat removal from the motor may, for example, be formed by the purge line or by the heat spreader as discussed above or below, by cooling fins attached to the motor housing or to the housing of the drive unit, or by a heat pipe connected with the motor in a thermally conductive manner. Further embodiments become apparent from the combinations of the aspects with one another and/or with the description above or below.

In particular, the present application, inter alia, further relates to the following aspects:

1. A method of operation of a heart assist device comprising an external drive unit and an implantable or implanted heart assist pump, wherein the drive unit comprises a motor for driving the heart assist pump, and wherein the motor is connected to the heart assist pump via a transcutaneous drive shaft, wherein the motor comprises a stator and a rotatably mounted rotor connectable to the drive shaft, wherein a fluid gap is formed between the rotor and the stator, wherein the fluid gap is in fluid connection with a purge opening for injecting a purge medium into the fluid gap, and wherein the heart assist device comprises a catheter surrounding the drive shaft, wherein a purge medium is injected into the fluid gap and into a space between the catheter and the drive shaft or into a lumen of the catheter.

2. The method of aspect 1, wherein a temperature of the purge medium in the fluid gap is at least 50° C., preferably at least 60° C., in a steady state of operation.

3. The method of any one of the previous aspects, wherein a temperature of the purge medium in the fluid gap is at most 100° C., preferably at most 90° C., in a steady state of operation.

4. The method of any one of the previous aspects, wherein the purge medium is a glucose solution or saline solution.

5. The method of any one of the previous aspects, wherein the drive unit comprises a purge line which is attached to the purge opening, wherein the purge line is in thermal contact with an outer surface of a motor housing and/or with an outer surface of a proximal section of the catheter, and wherein the purge medium is preheated by the thermal contact with the outer surface of the motor housing and/or with the outer surface of the proximal section of the catheter prior to injection of the purge medium into the fluid gap.

6. An external drive unit for an implantable heart assist pump comprising a motor for driving the heart assist pump, wherein the motor is connectable or connected to the heart assist pump via a transcutaneous drive shaft, wherein the drive unit comprises a heat pipe connected with the motor in a thermally conductive manner.

7. The drive unit of aspect 6, wherein the drive unit comprises a housing, in particular the motor housing or the housing of the drive unit, and wherein the heat pipe is connected with the housing in a thermally conductive manner.

8. A heart assist system comprising the drive unit of any one of aspects 6 or 7 and further comprising a console or a controller unit with a heat sink, wherein a portion of the heat pipe is connected with the heat sink in a thermally conductive manner to remove heat from the motor.

9. An external drive unit for an implantable heart assist pump comprising a motor for driving the heart assist pump, wherein the motor is connectable to the heart assist pump via a transcutaneous drive shaft, characterized by a heat spreader comprising a contact surface configured to contact a skin of a patient, wherein the contact surface is connected or connectable with the motor in a thermally-conductive manner to transfer heat generated by the motor to tissue of the patient.

10. A method of operation of a heart assist device comprising an external drive unit and an implantable or implanted heart assist pump, wherein the drive unit comprises a motor driving the heart assist pump, and wherein the motor is connected to the heart assist pump via a transcutaneous drive shaft, wherein the drive unit further comprises a motor housing, wherein the motor is arranged inside the motor housing, the drive unit further comprising a catheter surrounding the drive shaft and a purge line injecting a purge medium into a lumen of the catheter or into a space between the catheter and the drive shaft, wherein the purge line is in thermal contact with an outer surface of the motor housing and/or with an outer surface of a proximal section of the catheter such that heat is transferred from the outer surface of the catheter in the proximal section and/or from the outer surface of the motor housing to the purge medium.

11. The method of aspect 10, wherein the purge line guides the purge medium such that it first comes into thermal contact with the outer surface of the motor housing and/or with the outer surface of the proximal section of the catheter and is afterwards injected into the lumen of the catheter or into the space between the catheter and the drive shaft.

12. The method of aspect 11, wherein the purge line guides the purge medium such that it first comes into thermal contact with the outer surface of the motor housing and is afterwards injected into the lumen of the catheter or into the space between the catheter and the drive shaft.

13. The method of aspect 10, wherein the motor comprises a stator and a rotatably mounted rotor connected to the drive shaft, wherein a fluid gap is formed between the rotor and the stator, wherein the fluid gap is in fluid connection with a purge opening for injecting the purge medium into the fluid gap, wherein the purge line is connected to the purge opening.

14. The method of aspect 13, wherein the purge line and the fluid gap guide the purge medium such that it first comes into thermal contact with the outer surface of the motor housing and/or with the outer surface of the proximal section of the catheter, is afterwards injected into the fluid gap between the rotor and the stator, and is afterwards injected into the lumen of the catheter or into the space between the catheter and the drive shaft.

15. The method of aspect 13, wherein the purge medium flows in a distal direction in the fluid gap.

Figure 2:
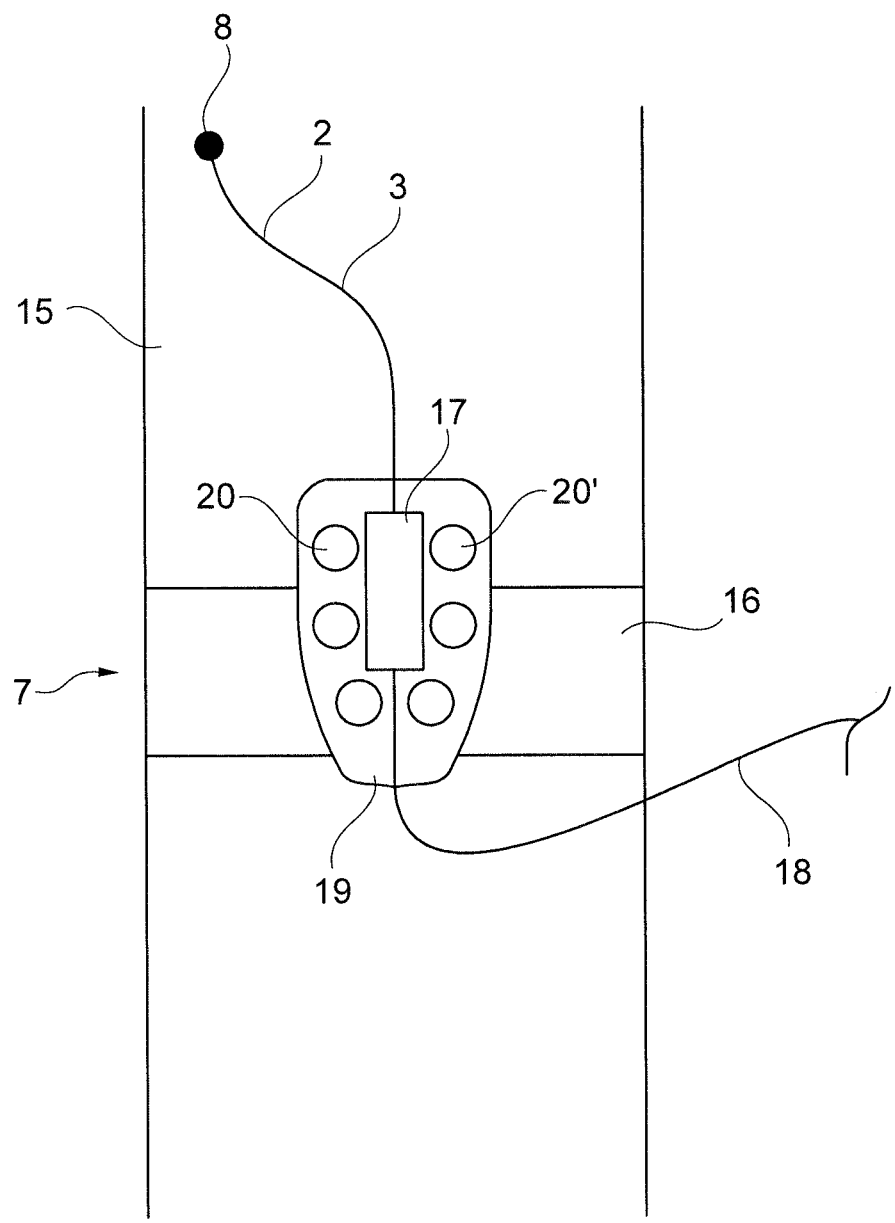
Figure 3:
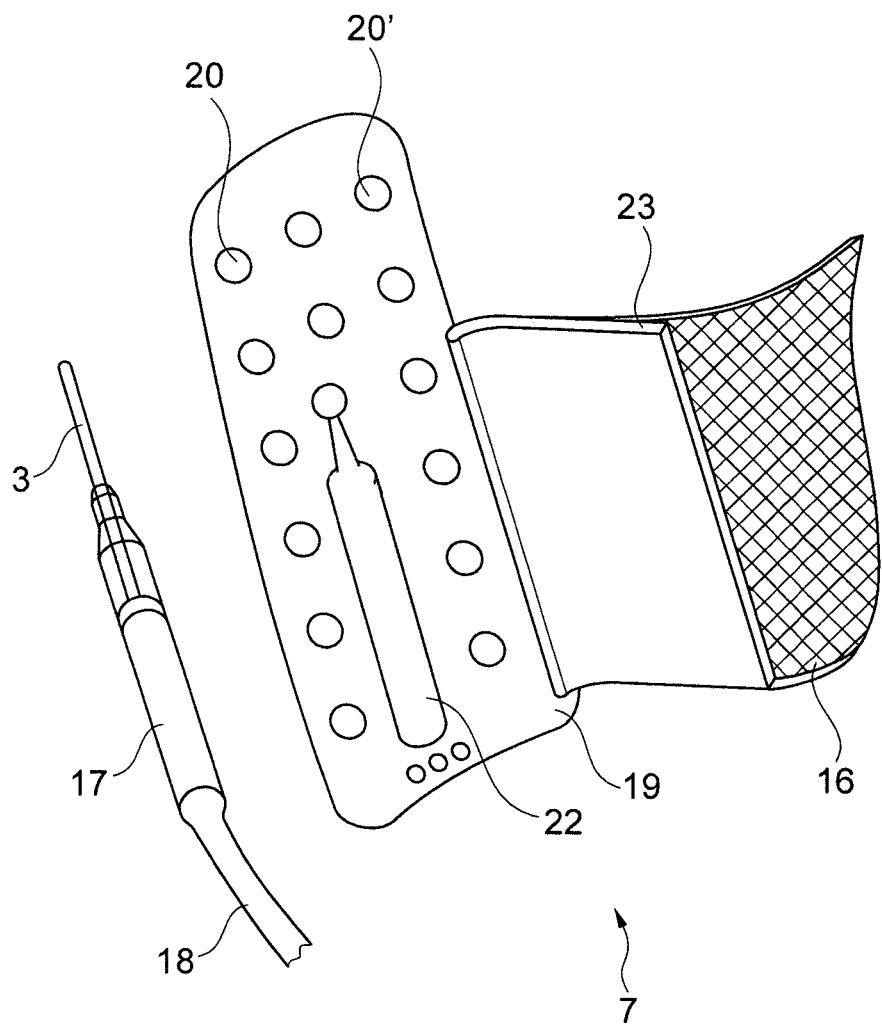
Figure 4:
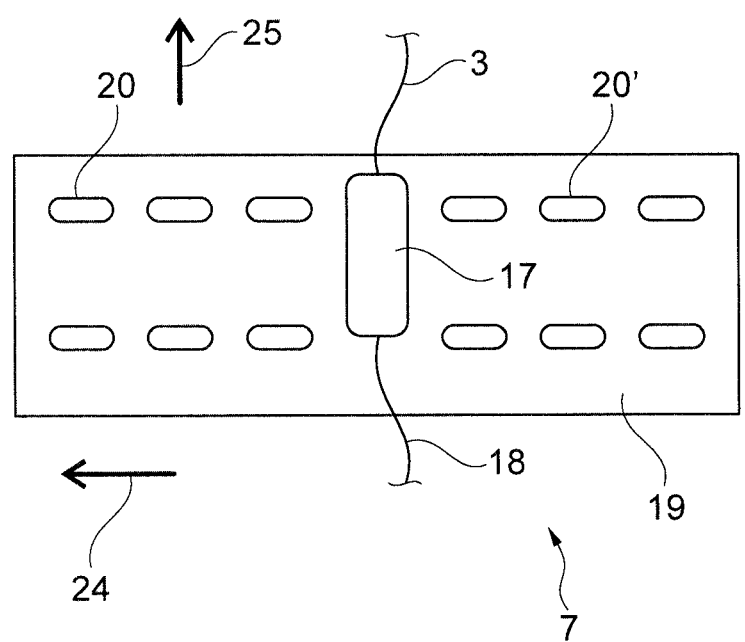
Figure 5:
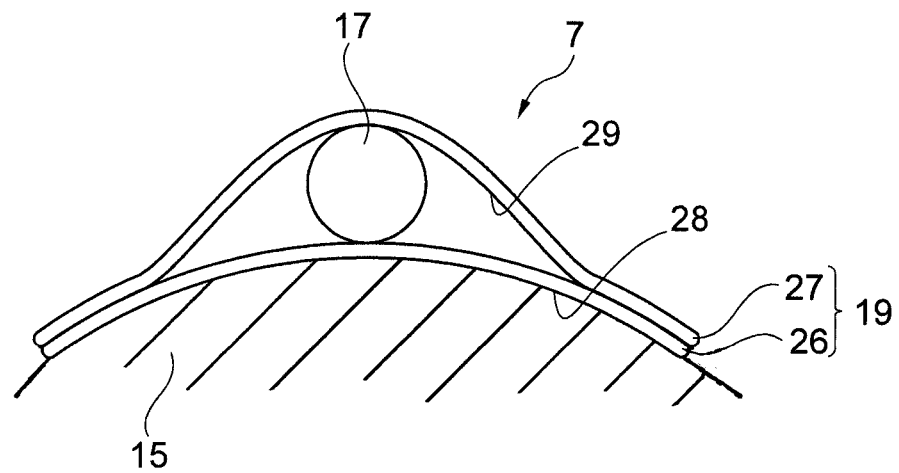
Figure 6:
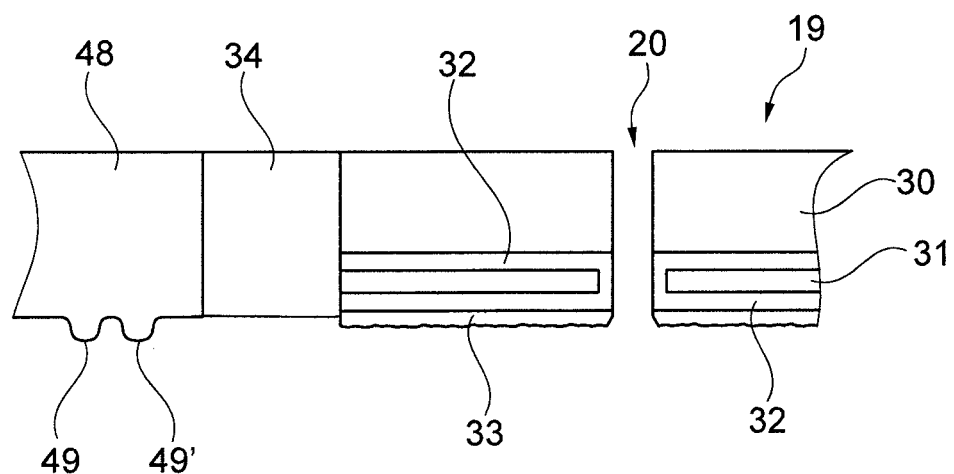
Figure 7:
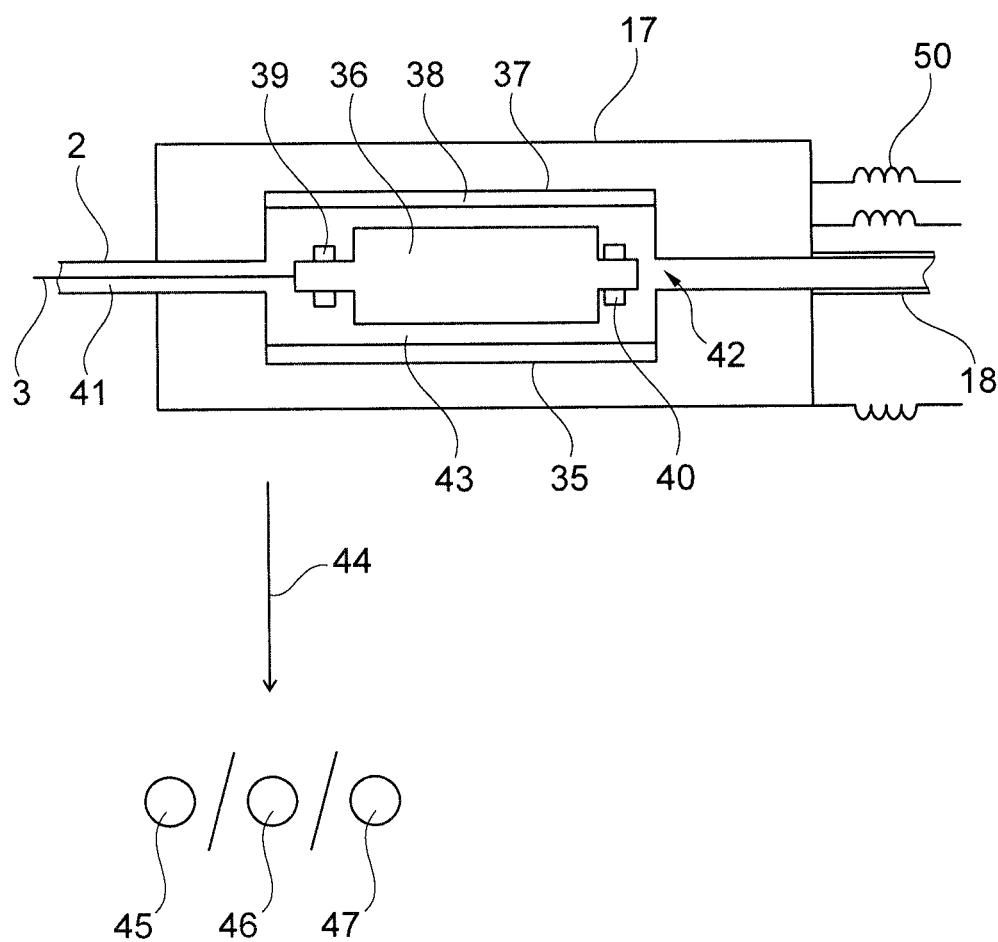
Figure 8:
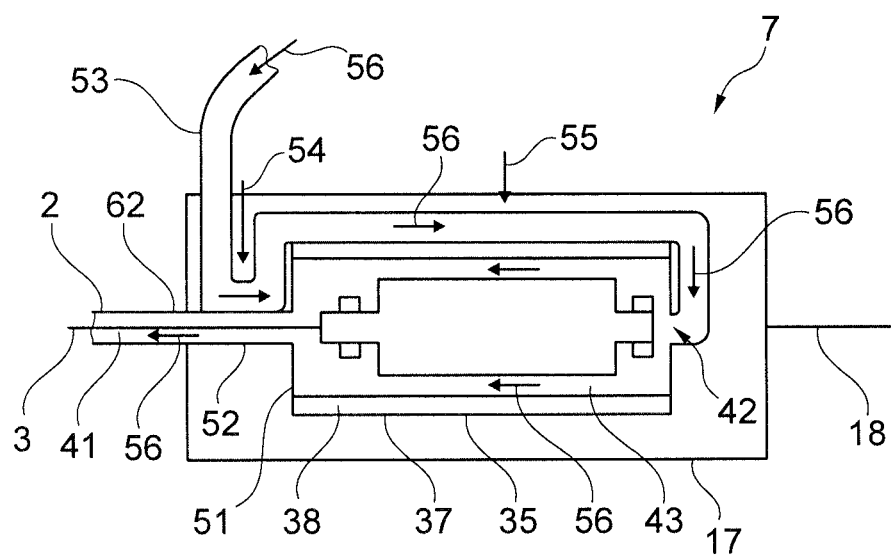
Figure 9:
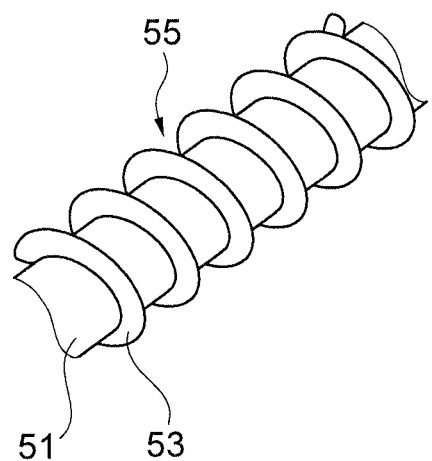
Figure 10:
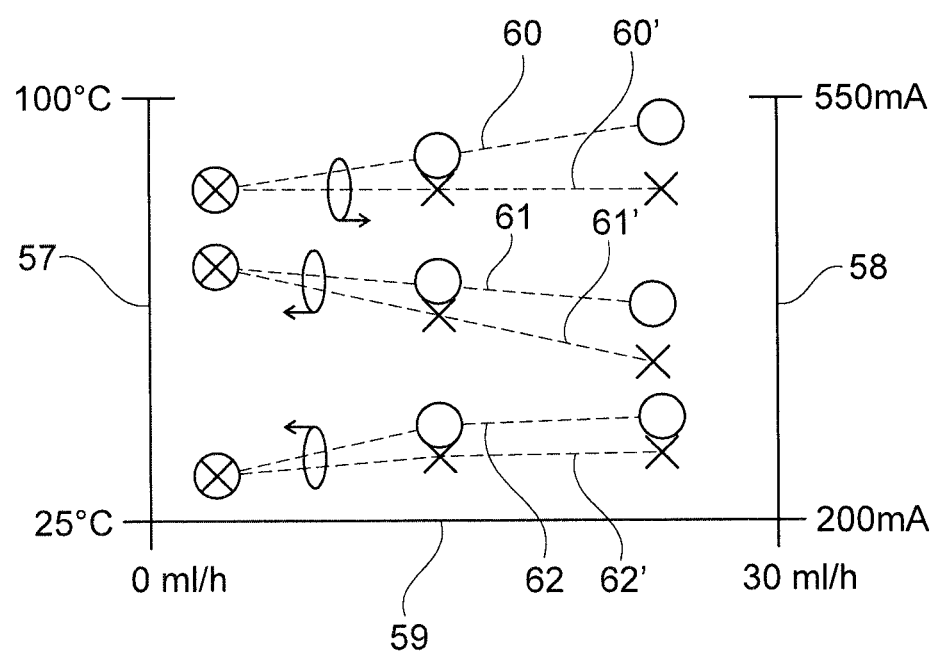
Figure 11:
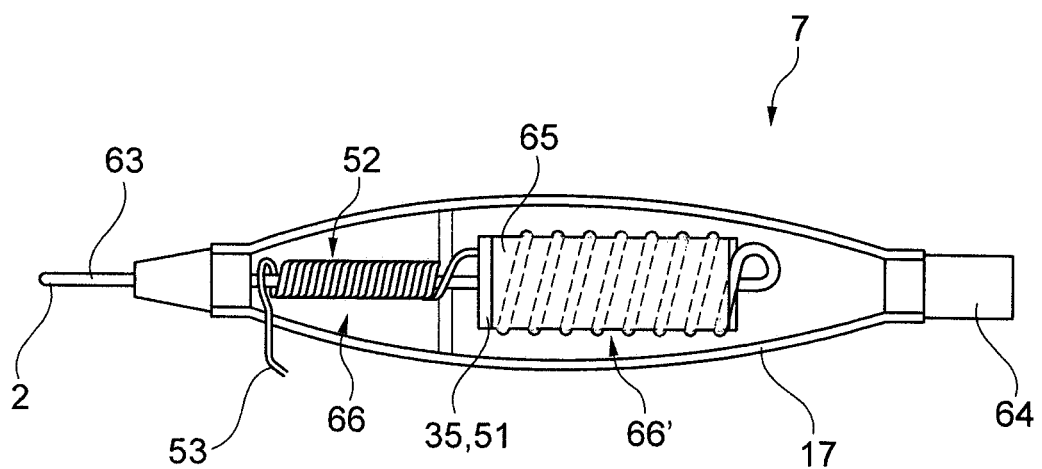

Exemplary embodiments will be described in conjunction with the following figures:

FIG. 1 a schematic representation of a heart assist device with an implanted heart assist pump and an extracorporal drive unit, FIG. 2 a schematic representation of the drive unit, FIG. 3 another schematic representation of the drive unit, FIG. 4 another schematic representation of the drive unit, FIG. 5 a schematic cross-sectional view of a heat spreader and a housing of the drive unit, FIG. 6 a schematic cross-sectional view of the heat spreader, FIG. 7 a schematic cross-sectional view of the housing of the drive unit and a motor, FIG. 8 a schematic cross-sectional view of a drive unit according to another embodiment, FIG. 9 a schematic perspective view of a purge line and a motor housing, FIG. 10 a graph showing a comparison of measured operating parameters for drive units with and without thermal contacts between the purge line and a motor housing as well as a proximal section of catheter, and FIG. 11 a schematic view of a drive unit according to another embodiment.

A schematic representation of a heart assist device 1 is depicted in FIG. 1. The heart assist device 1 comprises a catheter 2. A flexible drive shaft 3 is guided inside the catheter 2. Distal ends of the catheter 2 and the drive shaft 3 are connected with a pump head of a heart assist pump 4. The heart assist pump 4 comprises a housing 5 and a propeller 6. The propeller 6 is connected with a distal and of the drive shaft 3. A proximal end of the drive shaft 3 is connected with an extracorporal drive unit 7 comprising a motor. The drive unit 7 is configured to drive a rotary motion of the propeller for moving blood of a patient.

The heart assist pump 4 as well as the catheter 2 and the drive shaft 3 are inserted into the femoral artery of the patient via a puncture site 8 located in the groin of the patient. The depicted arrangement illustrates the use of heart assist device 1 to assist the left-ventricular function of the heart, wherein the heart assist pump 4 is partly arranged inside the left ventricle 10 of the patient in an area of the aortic valve 11. When the heart assist device 1 is operated, the drive shaft 3 is driven by the motor of the drive unit 7 and the heart assist device 1 conveys blood from the left ventricle 10 into the aorta 12, i.e., from a distal end 13 of the heart assist device 1 in a direction toward a proximal end 14. In other embodiments, the heart assist device 1 may be configured to convey blood in a direction from the proximal end 14 of the heart assist device 1 toward the distal end 13. Such an arrangement may be particularly suited for assisting a right-ventricular function of the heart.

The drive unit 7 may be attached to a thigh 15 of the patient, as depicted schematically in FIG. 2. Reoccurring features in FIG. 2 and in the following figures are denoted using the same reference numerals. In the depicted embodiment, the drive unit 7 is held in place with respect to the puncture site 8 by a strap 16, e.g., an elastic strap. In most embodiments, a length of the strap is between 45 and 60 cm. Other means of fixation are possible, however, as discussed below. The motor is arranged inside a motor housing. The motor housing is arranged inside a housing 17 of the drive unit 7, e.g., formed by an injection moulded ABS part. A surface of the housing 17 of the drive unit 7 is smooth and stepless in most embodiments so that the housing 17 of the drive unit 7 is easy to clean and may serve as a handle of the heart assist device 1. The catheter 2 is rigidly connected with a proximal end of the housing 17 of the drive unit 7 in a fluid-tight manner. Further, a supply line 18 is schematically shown in the figure. In the embodiment shown, the supply line 18 is connected with a proximal end of the housing 17 of the drive unit 7 and contains an electrical power supply line for the motor and a fluid supply or purge line for a purge medium. In other embodiments, the fluid supply or purge line and the power supply line are each guided inside one of multiple separate supply lines. Further, in some embodiments, the supply line 18 and/or the fluid supply or purge line exit the housing 17 of the drive unit 7 at a distal end or a side surface of the housing 17 of the drive unit 7.

The drive unit 7 further comprises a heat spreader 19. The heat spreader 19 is rigidly connected with the housing 17 of the drive unit 7 such that heat generated by the motor during operation is transferred to the heat spreader 19. The heat spreader 19 may be thin and have a thickness of 4 mm or less. For example, the heat spreader 19 may be formed by a patch as discussed below or by a flat, two-dimensional heat pipe. A bottom surface of the heat spreader 19 lies flat against and is in direct contact with the skin of the patient in a contact surface so that heat may be transferred from the heat spreader 19 to tissue of the patient. During operation of the motor a temperature of the outer surface of the housing 17 of the drive unit 7 may exceed 43° C. before fixation of the heat spreader 19 to the thigh 15. However, the heat conductivity of the heat spreader 19 ensures that the heat is evenly spread over a sufficient area and transferred into the thigh 15 so that the temperature at the surface of the housing 17 of the drive unit 7 decreases rapidly under a temperature of 42° C., which defines a critical temperature for damaging the tissue.

The heat spreader 19 comprises regions with a thermal conductivity of more than 100 W/(m·K) to spread the heat laterally so that the heat is efficiently transferred to the entire contact surface. A surface area of the contact surface may be as large as 200 cm² in some embodiments. The heat spreader 19 further comprises openings (through holes), two of which are denoted using the reference numerals 20 and 20'. The openings 20, 20' allow for a transfer of vaporized sweat to ambient air and hence increase a comfort of wear.

A perspective view of the drive unit 7 is shown in FIG. 3. In the depicted embodiment, the heat spreader 19 has a recess 22 for receiving the housing 17 of the drive unit 7. The strap 16 comprises a hook and loop fastening mechanism with a looped surface 23 for engaging a corresponding hooked surface disposed at an end portion of the strap and not depicted in the figure. When the heart assist device 1 is in use, the housing 17 of the drive unit 7 is received in the recess 22, and the strap 16 is circumferentially wrapped around the thigh such that the housing 17 of the drive unit 7 is covered by a portion of the strap 16, and the drive unit 7 is held in place.

The openings 20, 20' of the heat spreader 19 may be elongated, as schematically depicted in FIG. 4. In this case, the openings 20, 20' exhibit a larger diameter in a circumferential direction 24 with respect to the thigh 15 to enable an efficient heat transport of the heat spreader 19 in this direction 24. The housing 17 of the drive unit 7 is elongated in a perpendicular direction 25 corresponding to an axial direction 25 of the thigh 15.

The heat spreader 19 may be curved and/or flexible to adapt to a shape of the thigh 15. For example, the heat spreader 19 may comprise a foil or a patch. FIG. 5 depicts an exemplary cross section through a heat spreader 19 formed by a first patch 26 and a second patch 27 and the housing 17 of the drive unit 7. The patches 26, 27 are each bendable and each comprise adhesive bottom surfaces 28, 29 facing the thigh 15. The patches 26, 27 enclose the housing 17 of the drive unit 7 in the depicted embodiment to efficiently draw heat from the motor. In the depicted embodiment, the adhesive surfaces of the heat spreader 19 form a holding means to hold the drive unit 7 in place with respect to the puncture site 8. Therefore, another holding means, such as the strap 16 described above, may not be necessary, but may still be supplied in some embodiments.

An exemplary cross section through the heat spreader 19 is shown in FIG. 6. The heat spreader 19 may be a multi-layered structure. The heat spreader 19 comprises carrier layer 30 that forms the top layer of the heat spreader 19.

The carrier layer 30 may be formed by an elastomeric and/or plastic material. For an efficient heat transfer across the area of the contact surface, i.e., in a horizontal direction in the figure, the heat spreader 19 further comprises a thin thermally conductive layer 31, which may be formed by a thin layer of a material with a high thermal conductivity, e.g., copper, aluminium or pyrolytic carbon. The thermally conductive layer 31 is enclosed on either side by an inert and biocompatible coating 32 made of parylene, polyurethane, silicone, PEEK, or a biocompatible, for example an implantable metal. The biocompatible coating 32 further covers the thermally conductive layer 31 on inner walls of an opening 20 of the heat spreader 19. A stepless bottom surface of the heat spreader is formed by an adhesive layer 33, e.g., containing glue, to stick the heat spreader 19 to the skin of the patient.

Further, a sweat absorbent portion 34 of the heat spreader 19 or of the drive unit 7 is schematically depicted in FIG. 6. The sweat absorbent portion may, e.g., be made of textile and/or cotton. In addition, the heat spreader 19 or the drive unit 7 comprises a rubberized area 48 with rubber nubs 49, 49' to prevent the heat spreader 19 from sliding relative to the puncture site 8. The sweat absorbent portions 34 and the rubberized areas 48 may be distributed evenly across the bottom surface of the heat spreader 19.

A schematic view of the motor 35 is shown in FIG. 7. The motor 35 is arranged inside the motor housing which is arranged in the housing 17 of the drive unit 7. The motor 35 comprises a rotor 36 with a permanent magnet and a stator 37 with windings 38. The rotor 36 is rotatably mounted using a first bearing 39 and a second bearing 40 and may be rotated upon current flow through the windings of the stator 37. The rotor 36 is rigidly connected with the drive shaft 3 to drive the propeller 6.

The catheter 2 is rigidly connected with the housing 17 of the drive unit 7, and a space 41 is formed between the catheter 2 and the drive shaft 3. This space 41 is in fluid connection with a fluid gap 43 formed between the rotor 36 and the stator 37, with a purge opening 42, and with the supply line 18. A width of the fluid gap 43 in a radial direction may be between 0.2 and 0.3 mm. When the heart assist device 1 is operated, a purge medium, e.g., a glucose solution, is supplied via the supply line 18 and flows through the fluid gap 43 and through the space 41 between the catheter 2 and the drive shaft 3 (and eventually into the patient at a proximal end of the heart assist device 1).

During operation of the motor 35 a power dissipation of, e.g., 2 W may cause the motor 35 to heat up. The heat is removed from the motor 35 as schematically indicated by the arrow with the reference numeral 44 to keep a temperature of the glucose solution inside the fluid gap 43 constant at 75° C. in a steady state of operation. To remove the heat, the heat may, for example, be transferred to tissue 45 of the patient using the heat spreader 19 as discussed above, to ambient air 46, e.g., using cooling fins on the housing 17 of the drive unit 7, and/or to a heat sink 47 of a console or a controller unit, e.g., via an elongated heat pipe connected to the housing 17 of the drive unit 7. Further, additionally or alternatively, the heat may be transferred to the fluid supply line or purge line as described below. Any combinations of these heat removal mechanisms are possible.

Further, inductors 50 may be supplied to reduce the eddy-current losses when the motor 35 is not driven in full block commutation. These inductors 50 can also be located inside the housing 17 of the drive unit 7, but in a preferred embodiment the inductors 50 are located at the end of the motor cable 18 which is connected to the controller unit of the motor 35 (or in the controller unit itself) to avoid additional weight and heat sources at the motor 35 and at the patient's leg.

Heat removal to the purge line is described in conjunction with the following figures. FIG. 8 schematically depicts another embodiment of the drive unit 7. This drive unit 7 may comprise any of the features of the previously described drive unit 7. Further, in the drive unit 7 of FIG. 8, a purge line 53 acts in a double role, namely as a supply line for the purge medium and as a means for heat removal. As shown in FIG. 8, the windings 38 of the stator 37 are enclosed in the motor housing 51. The motor housing 51 is arranged in a central position within the housing 17 of the drive unit 7. In other embodiments, however, the motor housing 51 is arranged in a proximal position within the housing 17 of the drive unit 7. Further, the catheter 2 comprises a proximal section 52, which is arranged inside the housing 17 of the drive unit 7. As schematically shown, the supply line 18 is attached to the proximal end of the housing 17 of the drive unit 7. The supply line 18 contains electrical leads for the electrical supply of the motor 35. The purge line 53 is not contained within the supply line 18 in this embodiment. The purge line 53 extends through an opening in a side surface of the housing 17 of the drive unit 7 in a distal region of the housing 17 of the drive unit 7.

An end portion of the purge line 53 is attached to a supply of a purge medium (not shown). The purge line 53 extends into an interior of the housing 17 of the drive unit 7. Inside the housing 17 of the drive unit 7, the purge line 53 lies against an outer surface of the proximal section 52 of the catheter 2. Thereby, a thermal contact between the proximal section 52 of the catheter 2 and the purge line 53 is formed, as indicated by an arrow with reference sign 54. Further, the purge line 53 lies against an outer surface of the motor housing 51. Thereby, a thermal contact between the motor housing 51 and the purge line 53 is formed, as indicated by an arrow with reference sign 55. The purge line 53 is further attached to the purge opening 42. When the purge medium is supplied it flows through the drive unit 7 as indicated by arrows (some of which are marked by reference sign 56). The purge medium first passes the regions of thermal contact 54, 55, then enters the fluid gap 43 and afterwards enters the space 41 between the catheter 2 and the drive shaft 3. In further embodiments, the purge medium enters a lumen of the catheter 2. The purge medium flows mainly in a proximal direction when passing the thermal contacts 54, 55. Later, when the purge medium flows through the fluid gap 43 and the space 41 between the catheter 2 and the drive shaft 3, the purge medium flows in a distal direction.

During operation of the heart assist pump, the injected purge medium cools the proximal section 52 of the catheter 2 and the motor 35 due to the thermal contacts 54, 55 and due to its comparatively low temperature. Thereby, a section 63 of the catheter 2, which is arranged distally adjacent to the proximal section 52 of the catheter 2 and which is arranged outside of the housing 17 of the drive unit 7 is significantly cooled, such that the section 63 of the catheter 2 that is not arranged inside the housing 17 of the drive unit 7 may be touched without a risk of injury. Further, a risk of deformation of the catheter 2 (and thereby a risk of deformation and failure of the flexible drive shaft 3 arranged inside the catheter 2) due to a heat up of the section 63 of the catheter 2 is reduced. Further, the purge medium is preheated due to the thermal contacts 54, 55 prior to entering the fluid gap 43. As a consequence, the purge medium enters the fluid gap 43 with a higher temperature and a lower viscosity, so that friction losses in the motor 35 are reduced and the motor 35 operates more efficiently.

The motor housing 51 has a cylindrical shape in most embodiments. As shown in FIG. 9, the purge line 53 has a tubular shape and is wrapped around the motor housing 51 such that the purge line 53 directly contacts the outer surface of the motor housing 51 to enable a good thermal contact 55. Further, the purge line 53 may be wrapped around the proximal section 52 of the catheter 2 in a similar manner. To fabricate the drive unit 7, the purge line 53 may be preformed by thermoforming to create the spiraling shape of the purge line 53. After the purge line 53 is wrapped around the proximal section 52 of the catheter 2 and around the motor housing 51, the purge line 53 may be embedded into a flexible silicone casting material or fixly secured to the motor housing 51 by a shrink tube surrounding the purge line 53 or by an adhesive arranged between the motor housing 51 and the purge line 53. The proximal section 52 of the catheter 2 also has a cylindrical shape in most embodiments. A diameter of the purge line 53 may be uniform. The catheter 2 and in particular its proximal section 52 may comprise a plastic material, e.g., PU or polyether block amide (PEBA), e.g., Pebax®. The catheter 2 may be braided with a metal.

The drive unit 7 may further comprise a thermal insulation arranged between the purge line 53 and the housing 17 of the drive unit 7 (not shown), so that the housing 17 of the drive unit 7 is prevented from heating up. Further, an efficiency of the heat exchangers formed by the thermal contacts 54, 55 may be improved in this way. The thermal insulation may fully surround the purge line 53 in the regions of thermal contact 54, 55 and may be an insulating foam tube made from a plastic material. The thermal insulation may also be formed by an air gap between the purge line 53 and the housing 17 of the drive unit 7.

FIG. 10 shows a graph of measured operational parameters for different heart assist devices 1: the first with a drive unit 7 according to FIG. 8, i.e., comprising the thermal contacts 54, 55 (crosses), and the second with a corresponding drive unit 7 for which, however, the purge line 53 is neither in thermal contact with the proximal section 52 of the catheter 2 nor with the motor housing 51 (circles). The left vertical axis 57 indicates temperatures while the right vertical axis 58 indicates the motor current that has to be applied in order to achieve a predefined blood transfer rate. The horizontal axis 59 indicates the flow rate of the purge medium. The topmost measurement values 60, 60' correspond to the right vertical axis denoting the motor current. The intermediate 61, 61' and lowest 62, 62' measurement values correspond to the left vertical axis and denote a temperature 61, 61' of the motor 35 and a temperature 62, 62' of the section 63 of the catheter 2, which is arranged adjacent to the proximal section 52 of the catheter 2. The motor temperature 61, 61' decreases with increasing purge rate, while the temperature 62, 62' of the section 63 of the catheter 2 increases with increasing purge rate. The measurement values show that both the motor as well as the section 63 of the catheter 2 can be effectively cooled by using the proposed thermal contacts 54, 55 of the purge line with the motor housing 51 and with the proximal section 52 of the catheter 2. The motor current 60 increases with the purge rate when thermal contacts 54, 55 are not provided. In contrast, when the proposed thermal contacts 54, 55 are used, the motor current 60' can be significantly reduced at reasonable purge rates. Hence, the proposed thermal contacts 54, 55 make the heart assist device 1 more efficient. Surprisingly, due to the thermal contacts 54, 55 the motor current 60' does not depend on the flow rate at all. Hence, an influence of the purge rate on the motor current 60' may be neglected, when the motor current 60' is used as an important control parameter of the heart assist device 1 (e.g., indicating malfunction of the heart assist device 1). Therefore, the proposed thermal contacts 54, 55 enable a simplified monitoring circuitry of the heart assist device 1.

FIG. 11 shows a drive unit 7 according to another embodiment. This drive unit 7 may comprise any or all of the features described above. An upper portion of the housing 17 of the drive unit 7 is not shown in the figure so that an interior of the drive unit 7 is visible. The housing 17 of the drive unit 7 serves as a handle of the drive unit 7 and for this reason exhibits a curved shape that may be held easily with one hand. The supply line 18 (not shown) comprising the electrical leads for the power supply of the motor may be attached to a supply plug 64 disposed at a proximal end of the housing 17 of the drive unit 7. Further electrical leads (not shown for clarity) connect the supply line with the motor 35, which is arranged inside the motor housing 51. The catheter 2 comprises the section 63 which is arranged adjacent to and outside of the housing 17 and further comprises the proximal section 52, which is arranged inside the housing 17 and which connects the section 63 with the motor 35.

The purge line 53 enters the housing 17 of the drive unit 7 in a distal section of the housing 17. In addition, the purge line 53 is wrapped around the proximal section 52 of the catheter 2 as well as the motor housing 51 to form the thermal contacts 54, 55, as described above. The purge line 53 is further connected with a proximal end of the motor housing 51 to form the fluid connection with the fluid gap 43 of the motor 35. To further improve the thermal contact of the purge line 53 with the motor housing 51 the purge line 53 is enclosed within a heat-shrink tubing 65 (the position of the purge line 53 underneath the heat-shrink tubing 65 is illustrated using dashed lines). The heat-shrink tubing 65 pushes the purge line 53 against the motor housing 51, thereby improving the thermal contact. The portion of the purge line 53 that is wrapped around the proximal section 52 of the catheter 2 may also be enclosed within a heat-shrink tubing (not illustrated). Further, air gaps 66, 66' are formed between the housing 17 of the drive unit 7 and the portions of the purge line 53 that form the thermal contacts 54, 55 with the motor housing 51 and the proximal section 52 of the catheter 2. The air gaps 66, 66' form a thermal insulation to the motor housing 51 (insulating foam tubes as described above may be alternatively or additionally be provided). Further, the air gaps 66, 66' allow the heat generated by the motor to distribute within the housing 17 to some extent by convection so that local hot spots are avoided.

The invention claimed is:

1. An external drive unit for an implantable heart assist pump comprising:
    an external drive unit housing comprising:
        a motor housing arranged inside the external drive unit housing;
        a drive shaft, wherein the drive shaft is transcutaneous;
        a motor for driving a heart assist pump, wherein the motor is configured to connect to the heart assist pump via the drive shaft and wherein the motor is arranged inside the motor housing; and
        a catheter surrounding the drive shaft; and
    a purge line for injecting a purge medium into a lumen of the catheter or into a space between the catheter and the drive shaft,
    wherein the purge line extends through an opening in a side of the external drive unit housing and extends between the external drive unit housing and the motor housing wherein the purge line is in thermal contact with at least one of an outer surface of the motor housing or an outer surface of a proximal section of the catheter, and
    wherein at least one of the motor housing or the proximal section of the catheter are arranged within the external drive unit housing.

2. The external drive unit of claim 1, wherein the purge line is configured to guide the purge medium such that:
    the purge medium first comes into thermal contact with at least one of the outer surface of the motor housing or the outer surface of the proximal section of the catheter, and
    the purge medium is afterwards injected into the lumen of the catheter or into the space between the catheter and the drive shaft.

3. The external drive unit of claim 2, wherein the purge line is in thermal contact with both the outer surface of the motor housing and the outer surface of the proximal section of the catheter.

4. The external drive unit of claim 3, wherein the purge line is fully extracorporeal.

5. The external drive unit of any of claim 4, wherein the purge line is configured to guide the purge medium such that:
    the purge medium first comes into thermal contact with the outer surface of the proximal section of the catheter, and
    the purge medium afterwards comes into thermal contact with the outer surface of the motor housing.

6. The external drive unit of claim 1, wherein the motor comprises a stator and a rotor connected to the drive shaft, wherein the rotor is rotatably mounted and wherein a fluid gap is formed between the rotor and the stator, wherein the fluid gap is in fluid connection with a purge opening for injecting the purge medium into the fluid gap, and wherein the purge line is configured to connect to the purge opening.

7. The external drive unit of claim 6, wherein the purge line and the fluid gap are configured to guide the purge medium such that:
    the purge medium first comes into thermal contact with at least one of the outer surface of the motor housing or the outer surface of the proximal section of the catheter,
    the purge medium is afterwards injected into the fluid gap between the rotor and the stator, and
    the purge medium is afterwards injected into the lumen of the catheter or into the space between the catheter and the drive shaft.

8. The external drive unit of claim 1, wherein the purge line is configured to guide a flow of the purge medium in a proximal direction in an area in which the purge line is in thermal contact with at least one of the outer surface of the motor housing or the outer surface of the proximal section of the catheter prior to injection of the purge medium into the lumen of the catheter or into the space between the catheter and the drive shaft.

9. The external drive unit of claim 1, wherein the purge line encircles at least one of the motor housing or the proximal section of the catheter in an area in which the purge line is in thermal contact with at least one of the outer surface of the motor housing or the outer surface of the proximal section of the catheter.

10. The external drive unit of claim 9, wherein the purge line runs around at least one of the motor housing or the proximal section of the catheter in a helical manner in the area in which the purge line is in thermal contact with at least one of the outer surface of the motor housing or the outer surface of the proximal section of the catheter.

11. The external drive unit of claim 10, wherein the purge line runs around the proximal section of the catheter in a helical manner in the area in which the purge line is in thermal contact with the outer surface of the proximal section of the catheter.

12. The external drive unit of claim 1, wherein an overall thermal conductance between an interior surface of the purge line and an interior surface of the motor housing may amount to at least five times an overall thermal conductance between the interior surface of the purge line and an interior surface of the external drive unit housing.

13. The external drive unit of claim 12, wherein the overall thermal conductance between the interior surface of the purge line and the interior surface of the motor housing may amount to at least ten times the overall thermal conductance between the interior surface of the purge line and the interior surface of the external drive unit housing.

14. The external drive unit of claim 1, wherein a part of the purge line runs between the motor housing and the external drive unit housing.

15. The external drive unit of claim 1, wherein a part of the purge line runs between the proximal section of the catheter and the external drive unit housing.

16. The external drive unit of claim 1, further comprising a thermal insulator arranged between the purge line and the external drive unit housing.

17. The external drive unit of claim 1, further comprising a heat spreader comprising a contact surface configured to contact a skin of a patient, wherein the contact surface is configured to connect with the motor in a thermally-conductive manner to transfer heat generated by the motor to tissue of the patient.

18. The external drive unit of claim 17, wherein the heat spreader is flexible at least in an area.

* * * * *

UNITED STATES PATENT AND TRADEMARK OFFICE
CERTIFICATE OF CORRECTION

PATENT NO. : 11,986,609 B2
APPLICATION NO. : 16/603527
DATED : May 21, 2024
INVENTOR(S) : Spanier et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1154 days.

Signed and Sealed this
Twelfth Day of August, 2025

Coke Morgan Stewart
*Acting Director of the United States Patent and Trademark Office*